US006126624A

United States Patent [19]
Frauenberger et al.

[11] Patent Number: 6,126,624
[45] Date of Patent: Oct. 3, 2000

[54] ORTHOTIC DEVICE FOR ABDUCTION

[76] Inventors: Karl-Andreas Frauenberger, Rennpaul 7; Amir Said Behfar, Rennpaul 6, both of D-30938 Burgwedel, Germany

[21] Appl. No.: 09/256,469

[22] Filed: Feb. 23, 1999

[30] Foreign Application Priority Data

Aug. 24, 1996 [DE] Germany .......................... 296 14 739

[51] Int. Cl.[7] ...................................................... A61F 5/00
[52] U.S. Cl. ............................................... 602/23; 602/24
[58] Field of Search ............................... 602/5, 19, 23–29

[56] References Cited

U.S. PATENT DOCUMENTS

| | | |
|---|---|---|
| 1,843,333 | 2/1932 | McCraken . |
| 2,588,411 | 3/1952 | Robinson ................................. 602/24 |
| 2,815,021 | 12/1957 | Freeman . |
| 2,963,020 | 12/1960 | Moran . |
| 3,892,231 | 7/1975 | Tummillo . |
| 4,576,151 | 3/1986 | Carmichael ............................... 602/24 |
| 5,362,305 | 11/1994 | Varn . |
| 5,558,628 | 9/1996 | Bzoch ...................................... 602/24 |

FOREIGN PATENT DOCUMENTS

| | | |
|---|---|---|
| 2 321 267 | 3/1977 | France . |
| 26 10 669 | 9/1977 | Germany . |
| 94 17 112 | 4/1995 | Germany . |
| 44 38 068 | 5/1996 | Germany . |
| 21 33 289 | 7/1984 | United Kingdom . |

*Primary Examiner*—Michael A. Brown
*Attorney, Agent, or Firm*—Shlesinger, Arkwright & Garvey LLP

[57] ABSTRACT

Orthotic device for abduction for person affected by spasticity for placing between the knees and/or feet of patients. Viewed from above, this orthotic device consists of an approximately H-shaped structure with a central element, the length of which can be adjusted, with cross-pieces which can be movably attached by means of articulations at both ends of the central element. The length of the cross-pieces can also be adjusted and serve to support the knees and/or feet. The cross-pieces have support elements movably mounted by means of articulations, which are provided with cushions in the form of foam, gel, or air pillows. The support elements can be constructed as unitary rectilinear pieces or as unitary angular pieces. Preferably these support elements consist of parts which are connected to one another and to the cross-piece in a pivoting or articulated fashion. It is possible to regulate the two support elements with respect to one another in a position which is rectilinear or angular to any degree to improve the wearing comfort for a wide array of different lying and sitting positions of the person affected by spasticity. The orthotic device for abduction is simple and economical to construct and simple and secure to install, and can be utilized in a wide variety of situations.

25 Claims, 2 Drawing Sheets

ORTHOTIC DEVICE FOR ABDUCTION

CROSS-REFERENCE TO RELATED APPLICATIONS

This is a continuation of PCT/EP97/04537, filed Aug. 21, 1997, which claims the priority of German Application No. 296 14 739.7, filed Aug. 24, 1996, and each of which is incorporated herein by reference.

FIELD OF THE INVENTION

The invention concerns an orthotic device for abduction for spastic persons.

BACKGROUND OF THE INVENTION

Children with cerebral damages often develop tetraspacticity. This results in the contracture of the extremities. A contraction of the abduction of the legs results in considerable difficulties with regard to the hygiene of the genital area and may bring about a luxation of the hip joints.

Orthotic devices known to date are expensive and, as a rule, have to be tailor-made to suit the patient. Furthermore, they are elaborate in its application.

From U.S. Pat. No. 2,815,021 an orthotic device is known for abduction for patients after a hip joint operation, by which the healing process and the restoration of the joint is supposed to be facilitated. The orthotic device for abduction is attached to the feet or the lower legs and comprises an extendable rigid element of the turnscrew type, at both end of the element support elements are articulately provided for the feet or the lower leg.

From DE-A-44 38 068 an orthotic device is known for abduction to be used for children, whose hip joint has developed abnormally. This orthotic device for abduction comprises two U-shaped upper leg mountings which can be enclosed by a strap, which mountings are joined via ball joints to an adjustable spacer.

OBJECTS AND SUMMARY OF THE INVENTION

The object of this present invention is therefore to produce an orthotic device for abduction for spastic persons which can be manufactured simply and cost-effectively as well as is simple and reliable in their application and can be modified.

This objective is achieved by an orthotic device for abduction according to the invention for spastic persons that has support elements attachable to the legs, the support elements being displaceably connected with a longitudinally adjustable cross-piece, and the support elements being provided for the knee and/or foot joints. The support elements for the knee comprise two support elements parts which are joined pivotably or articulately with each other and with the cross piece.

Additional advantageous and useful developments of the invention are further described below.

The orthotic device for abduction has a simple construction, can be reliably applied, can be cost-effectively manufactured and offered. It has a modular construction by virtue of which it can be stored and packaged in a compact manner. The orthotic device for abduction is preferably adjustable, so that practically it "grows with " still growing patients, e.g. spastic children. The use of the orthotic device for abduction according to the invention limits only the bringing together of the knees and legs of the patients and leads to a reduction of tensions. The risk of luxation of the hip joints is reduced. The hygiene of the genital area will be facilitated.

In the following the invention is explained in detail based on an embodiment illustrated in the attached drawings.

BRIEF DESCRIPTION OF THE DRAWINGS

The same components in the figures are designated with the same reference numerals.

DETAILED DESCRIPTION OF THE INVENTION

Figure 1:
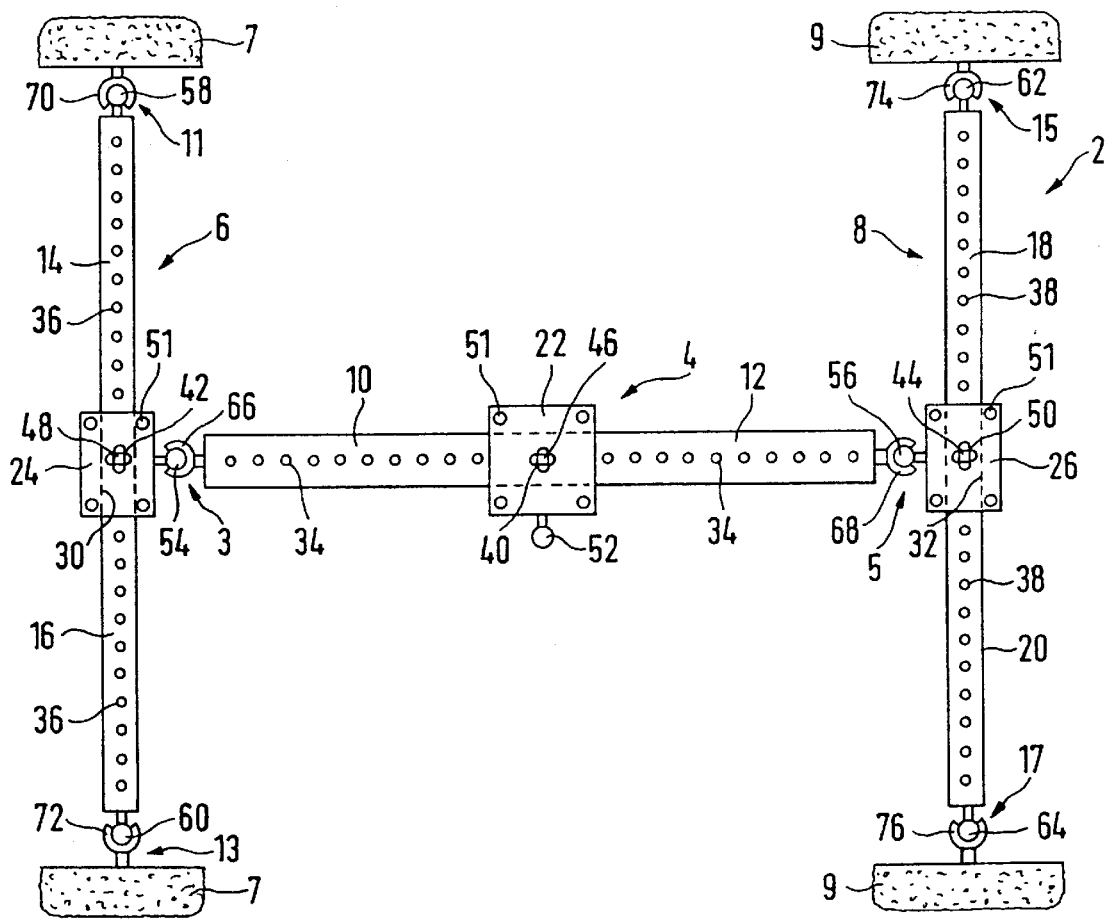
FIG. 1—a schematic illustration of an orthotic device for abduction, in top view, FIG. 2—a schematic perspective view illustrating a part of the orthotic device for abduction according to FIG. 1, FIGS. 3 and 4—two different support elements used for the orthotic device for abduction for the regions of the knee and/or foot joint, schematically illustrated, and FIG. 5—schematically illustrated a further embodiment of a support element for the regions of the knee and/or foot joint used in the orthotic device for abduction.
Figure 2:
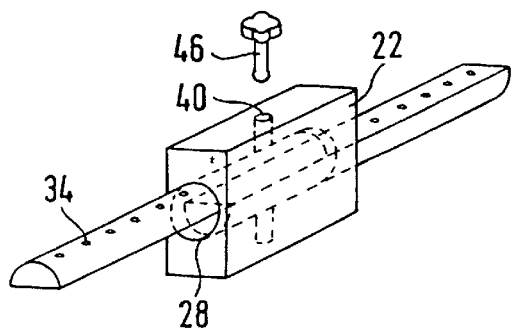

FIG. 1 illustrates an orthotic device 2 for abduction for spastic persons to be placed between the knees and/or feet of the patients. The orthotic device 2 for abduction comprises, when viewed from above, an approximately H-shaped structure with a longitudinally adjustable central piece 4 and with cross-pieces 6 and 8 displaceably attached to the ends of the central piece for up to and including three-dimensional movement by means of articulated joints 3, 5, which cross-pieces can also be adjusted longitudinally and serve the purpose of supporting the knee and/or foot joints.

The cross-pieces 6 and 8 have at both ends support elements 7, 9, displaceably attached by means of articulated joints 11, 13 and 15, 17 in the shape or, for example, cushions filled with foam, gel or air.

The central piece 4 and the cross-pieces 6 and 8 each comprise two rods 10, 12; 14, 16; 18, 20, which can be adjusted relative each other in the longitudinal direction and are mounted displaceably in adjusting and guide blocks 22, 24, 26, whose cross-section corresponds to the cross-section of the rods. The rods and the guide channels have preferably a rectangular, trapezoidal, semi-elliptic, triangular or dovetail-shaped cross-section, thus preventing a rotation of the rods in the adjusting and guide blocks. Each central piece and the cross-pieces may consist of two half-round rods positioned against each other with their flat sides, which may have, however, the disadvantage that the alignment of the holes in the rods and in the adjusting and guide blocks will be difficult due to their rotation in the adjusting and guide block.

The rods 10, 12, 14, 16, 18, 20 have spaced holes 34, 36, 38 which can be aligned with each other and with at least one hole 40, 42, 44 of the adjusting and guide blocks, into which lockable adjusting pins 46, 48 50 can be introduced to fix the respective adjusted length of the central piece and cross-pieces.

The adjusting and guide blocks 22, 24, 26 nay consist of two parts bolted together with bolts 51 or be made of one piece.

The adjusting and guide blocks 22, 24, 26 and the support elements 7, 9 may have for the articulate joints 3, 5 and 11, 13, 15, 17 similarly constructed first joint parts 52, 54, 56, 58, 60, 62, 64 and the rods 10, 12, 14, 16, 18, 20 of the central piece 4 and of the cross-pieces 6, 8 at their free ends may be similarly constructed second joint parts 66, 68, 70, 72, 74, 76 associated with the first joint parts and interacting with them.

By virtue of the above described modular construction the adjusting and guide blocks, the rods and the cushions can be interchanged and due to this modular construction only a minimum of components need to be manufactured and held in storage.

The central piece and the cross-pieces are made preferably of plastic material, e.g. polycarbonate.

Figure 3:
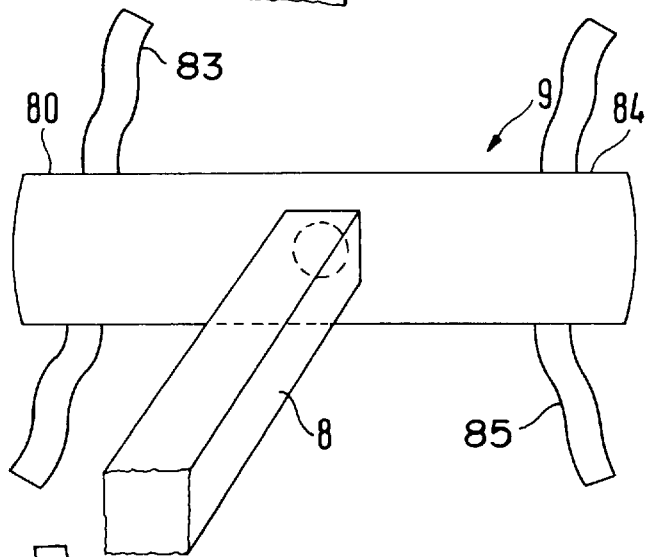
Figure 4:
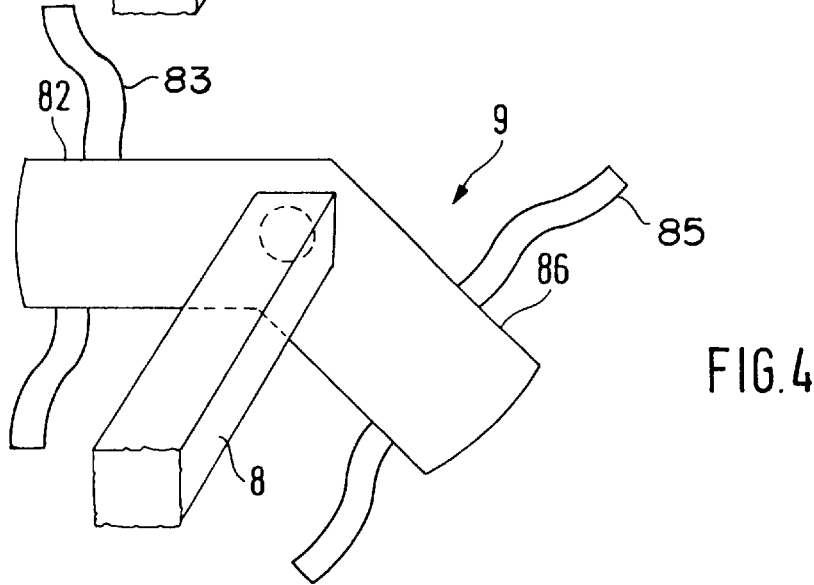

The support elements 9, particularly for the knee region, may have an integrated, straight construction, in particular for the stretched position of the legs or an integrated angular construction for the bent position of the knee, see FIGS. 3 and 4, wherein one end 80 or the side 82 of the support element is intended to guide the upper leg and the other end 84 or the other side 86 of the support element to guide the lower leg.

Figure 5:
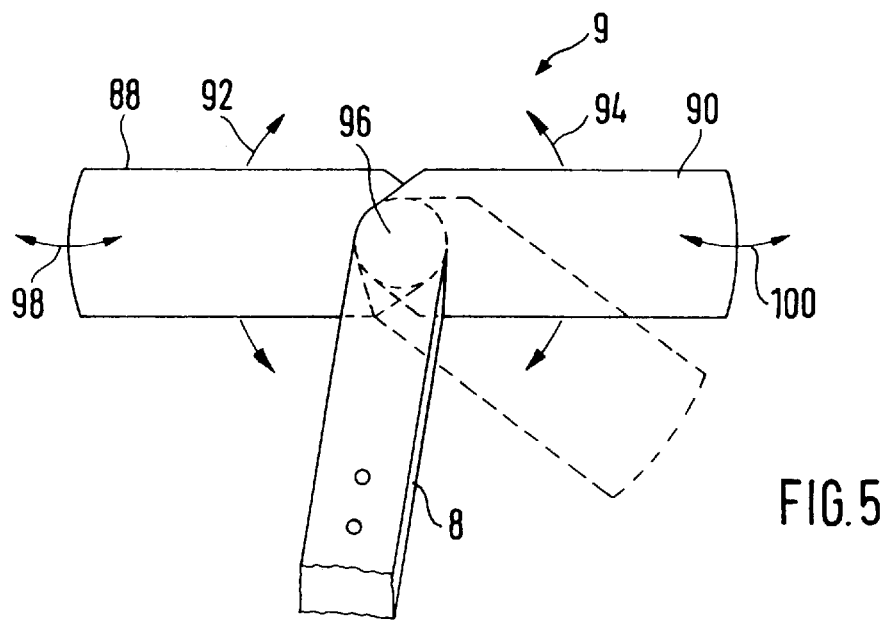

The support elements 9 comprise preferably two parts 88, 90, which are joined with each other and the cross-piece 8 pivotably or articulately and are provided preferably with cushions, see FIG. 5, wherein preferably both parts 88, 90 can be pivoted individually in a plane extending perpendicularly to the longitudinal axis of the cross-piece 8, see arrows 92 and 94 in FIG. 5, preferably about a common pivoting axis 96. By virtue of this the two support elements 88, 90 can be set relative each other in one straight line up to any angular position to improve the comfort of a spastic person in the most diverse lying and sitting positions.

In addition, a certain mobility of the support element parts 88, 90 in the direction of the cross-piece 8 may be provided to suit better the relevant anatomical situations, see arrows 98, 100, while the cushions provided allow already a certain mobility in this respect.

The support element parts 80, 82 have preferably a shell-shaped construction and have means for fastening on the upper and lower legs in the form of, for example, VELCRO-type straps (i.e., straps having hook-and-loop fasteners) 83, 85.

The orthotic device for abduction is used as follows;

First of all the length of the central piece 4 is adjusted to suit the distance between the knee and the foot joints. Afterwards the cross-pieces are placed with their support elements between the legs against the inside of the region of the knee and the region of the foot joint and fixed there, by means of VELCRO-type straps, for example. The extent of the abduction of the knees and feet can be adjusted by adjusting the length of the cross-pieces 6 and 8 .

By means of the modular construction of the orthotic device for abduction it is feasible to use the cross-pieces also without the central piece to abduct the knees only, in particular for small children, and/or only the feet.

While this invention has been described as having a preferred design, it is understood that it is capable of further modifications, and uses and/or adaptations of the invention and following in general the principal of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. An orthotic device for abduction, comprising:
   a) a pair of support elements, each of said support elements being connectable to a leg of a person;
   b) a cross-piece extending between and connecting said pair of support elements, said cross-piece being longitudinally adjustable;
   c) each said pair of support elements including at least a knee support element connectable in the region of a knee joint of a person;
   d) said knee support element including a first part and a second part, said second part being movable relative to said first part;
   e) said first part being disposed on one side of said cross-piece, and said second part being disposed on the other side of said cross-piece; and
   f) each said first and second parts being movable relative to said cross-piece.

2. A device as in claim 1, wherein:
   a) said pair of support elements includes at least a foot support element;
   b) a central piece joins said foot support element and said knee support element;
   c) a further cross-piece is provided between said knee support element and said central piece; and
   d) an articulated joint is provided between said rod-like central piece and said cross-piece, and a further articulated joint is provided between said central piece and said further cross-piece.

3. A device as in claim 2, wherein:
   a) each said central piece, said cross-piece, and said further cross-piece are longitudinally adjustable.

4. A device as in claim 2, wherein:
   a) each said central piece, said cross-piece, and said further cross-piece includes two rods longitudinally displaceable relative to each other;
   b) each of said two rods of each said central piece, said cross-piece, and said further cross-piece has a cross section; and
   c) a guide block having a guide channel corresponding to each one of the respective cross sections is provided on said central piece, said cross-piece, and said further cross-piece, and said guide block fixedly and detachably secures the respective rods.

5. A device as in claim 4, wherein:
   a) each of the rods has spaced apart holes which can be aligned with at least one corresponding hole provided in the guide block; and
   b) a locking pin is provided for the respective holes for fixing the respective lengths of the central piece, the cross-piece, and the further cross-piece.

6. A device as in claim 4, wherein:
   a) the guide block includes at least one of a one-piece construction and a two-piece construction including two parts which can be bolted together by bolts.

7. A device as in claim 4, wherein:
   a) the rods include half-round rods having flat sides, and the flat sides are positioned against each other.

8. A device as in claim 4, wherein:
   a) the cross-section of the rods and the cross-section of the guide channel prevent rotation of the rods in the guide block.

9. A device as in claim 8, wherein:
   a) the respective cross-sections of the rods and the guide blocks are one of rectangular, trapezoidal, semi-elliptic, triangular, and dovetail-shaped.

10. A device as in claim 1, wherein:
a) the first part guides an upper leg of a person and the second part guides the lower leg of the person when in use.

11. A device as in claim 1, wherein:
a) the first part guides an upper leg of a person and the second part guides the lower leg of the person when in use; and
b) the first and second parts are pivotable relative to each other within a plane extending substantially perpendicularly to the longitudinal axis of the cross-piece.

12. A device as in claim 1, wherein:
a) the first and second parts are pivotable about a common axis.

13. A device as in claim 1, wherein:
a) a pivot bearing is provided between the cross-piece and the knee support element; and
b) the first and second parts are pivotable about the pivot bearing in the direction of the cross-piece.

14. A device as in claim 1, wherein:
a) the knee support element has a shell-shaped construction.

15. A device as in claim 1, wherein:
a) each said pair of support elements includes at least one foot support element connectable to the leg of a person in the region of the foot;
b) a fastener is provided on the foot support element for fastening the foot support element to the leg of the person; and
c) a further fastener is provided on the knee support element for securing the knee support element to the leg of a person.

16. A device as in claim 1, wherein:
a) cushions are provided on the pair of support elements and the at least one knee support element, respectively.

17. A device as in claim 1, wherein:
a) each said pair of support elements includes at least one foot support element connectable in the region of a foot joint of a person.

18. An orthotic device for abduction, comprising:
a) a pair of support elements, each of said support element being connectable to a knee of a person;
b) a cross-piece extending between and connecting said pair of support elements, said cross-piece being longitudinally adjustable;
c) each said pair of support elements including a knee support element connectable in the region of a knee joint of a person;
d) said knee support element including a first part and a second part, said second part being movable relative to said first part;
e) each said first and second parts being movable relative to said cross-piece;
f) said pair of support elements including a foot support element connectable in the region of a foot joint of a person;
g) a central piece joining said foot support element and said knee support element;
h) a further cross-piece being provided between said knee support element and said central piece;
i) an articulated joint being provided between said central piece and said cross-piece and between said central piece and said further cross-piece;
j) each said central piece, said cross-piece, and said further cross-piece including two rods longitudinally displaceable relative to each other;
k) said two rods of each said central piece, said cross-piece, and said further cross-piece having a cross section; and
l) a guide block having a guide channel corresponding to each one of the respective cross sections, the guide block being provided on said central piece, said cross-piece, and said further cross-piece, and the guide block fixedly and detachably securing the respective rods.

19. A device as in claim 18, wherein:
a) each of the rods has spaced apart holes which can be aligned with at least one corresponding hole provided in the guide block; and
b) a locking pin is provided for the respective holes for fixing the respective lengths of the central piece, the cross-piece, and the further cross-piece.

20. A device as in claim 18, wherein:
a) the guide block includes at least one of a one-piece construction and a two-piece construction including two parts which can be bolted together by bolts.

21. A device as in claim 18, wherein:
a) the rods include half-round rods having flat sides, and the flat sides are positioned against each other.

22. A device as in claim 18, wherein:
a) the cross-section of the rods and the cross section of the guide channels prevent rotation of the rods in the respective guide blocks.

23. A device as in claim 22, wherein:
a) the respective cross-sections of the rods and the guide blocks are one of rectangular, trapezoidal, semi-elliptic, triangular, and dovetail-shaped.

24. An orthotic device for abduction, comprising:
a) a pair of support elements, each of said support element being connectable to a leg of a person;
b) a cross-piece extending between and connecting said pair of support elements, said cross-piece being longitudinally adjustable;
c) each said pair of support elements including at least a knee support element connectable in the region of a knee joint of a person;
d) said knee support element including a first part and a second part, said second part being movable relative to said first part;
e) each said first and second parts being movable relative to said cross-piece;
f) said pair of support elements including at least a foot support element connectable in the region of a foot joint of a person; and
g) a central piece joining said foot support element and said knee support element.

25. A device as in claim 24, wherein:
a) a further cross-piece is provided between said knee support element and said central piece; and
b) an articulated joint is provided between said central piece and said cross-piece, and a further articulated joint is provided between said central piece and said further cross-piece.

* * * * *